US010016129B2

(12) United States Patent
Versaci et al.

(10) Patent No.: US 10,016,129 B2
(45) Date of Patent: Jul. 10, 2018

(54) APPARATUS AND METHOD FOR MEASURING ABERRATIONS OF THE OPTICAL SYSTEM OF A LIVING BEING

(71) Applicant: Costruzioni Strumenti Oftalmici C.S.O. S.R.L., Scandicci (Florence) (IT)

(72) Inventors: Francesco Versaci, Prato (IT); Franco Giannozzi, Scandicci (IT); Gabriele Vestri, Florence (IT); Silvano Pieri, Sesto Fiorentino (IT)

(73) Assignee: COSTRUZIONI STRUMENTI OFTALMICI C.S.O. S.R.L., Scandicci (Florence) (IT)

( * ) Notice: Subject to any disclaimer, the term of this patent is extended or adjusted under 35 U.S.C. 154(b) by 81 days.

(21) Appl. No.: 15/025,916

(22) PCT Filed: Sep. 30, 2014

(86) PCT No.: PCT/IB2014/064958
§ 371 (c)(1),
(2) Date: Mar. 30, 2016

(87) PCT Pub. No.: WO2015/049632
PCT Pub. Date: Apr. 9, 2015

(65) Prior Publication Data
US 2016/0235293 A1  Aug. 18, 2016

(30) Foreign Application Priority Data
Oct. 2, 2013  (IT) ................ FI2013A0229

(51) Int. Cl.
A61B 3/14  (2006.01)
A61B 3/00  (2006.01)
(Continued)

(52) U.S. Cl.
CPC .......... *A61B 3/1015* (2013.01); *A61B 3/0025* (2013.01); *A61B 3/032* (2013.01);
(Continued)

(58) Field of Classification Search
CPC ............. G03F 7/70558; G03F 7/70741; G03F 7/7085; G03F 7/70916; G03F 7/70983;
(Continued)

(56) References Cited

U.S. PATENT DOCUMENTS

2003/0058403 A1* 3/2003 Lai ................ A61B 3/1015
351/212
2011/0234767 A1* 9/2011 Tokiwa ............ H04N 13/0217
348/47

FOREIGN PATENT DOCUMENTS

EP  2404546 A1  11/2012
WO  0158339 A2  8/2001
(Continued)

OTHER PUBLICATIONS

International Search Report for International Application No. PCT/IB2014/064958 (dated Jan. 13, 2015)(3 pages).

*Primary Examiner* — Brandi Thomas
(74) *Attorney, Agent, or Firm* — Lucas & Mercanti, LLP

(57) ABSTRACT

The present invention refers in general to the measurement of aberrations of the optical system of a living being, in particular a human. More specifically, the invention refers to methods and systems for reconstructing a wave front and/or for building a refractive error map.

7 Claims, 7 Drawing Sheets

(51) Int. Cl.
*A61B 3/10* (2006.01)
*A61B 3/032* (2006.01)
*A61B 3/103* (2006.01)
*A61B 3/12* (2006.01)
*G02B 27/10* (2006.01)

(52) U.S. Cl.
CPC ............... *A61B 3/103* (2013.01); *A61B 3/12* (2013.01); *A61B 3/14* (2013.01); *G02B 27/1066* (2013.01)

(58) Field of Classification Search
CPC .. G03F 7/70341; G03F 7/70591; G03F 7/706; G03F 7/70891; A61B 3/0025; A61B 3/032; A61B 3/1015; A61B 3/103; A61B 3/12; A61B 3/14
USPC ........ 351/200, 205, 206, 209–211, 221, 222, 351/243–246
See application file for complete search history.

(56) References Cited

FOREIGN PATENT DOCUMENTS

| WO | 02075367 A2 | 9/2002 |
|---|---|---|
| WO | 2004025352 A1 | 3/2004 |
| WO | 2011104062 A2 | 9/2011 |

\* cited by examiner

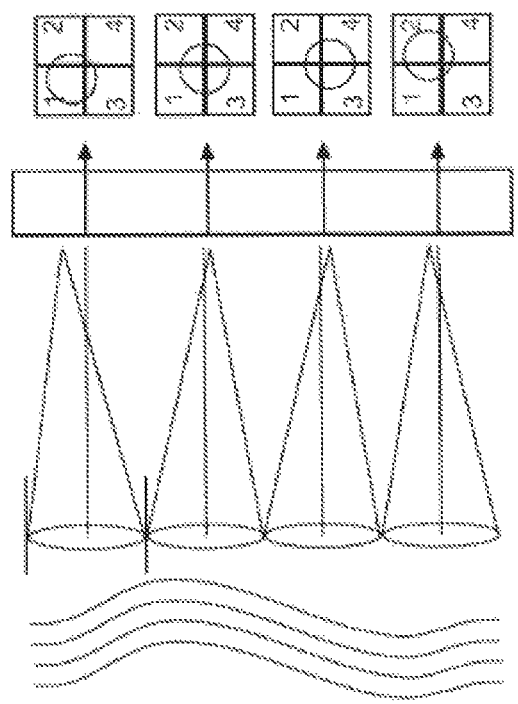
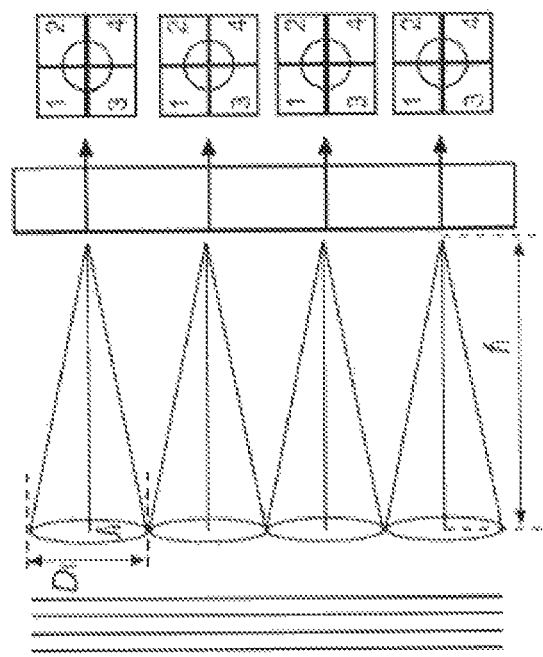
Fig. 2b
Fig. 2a

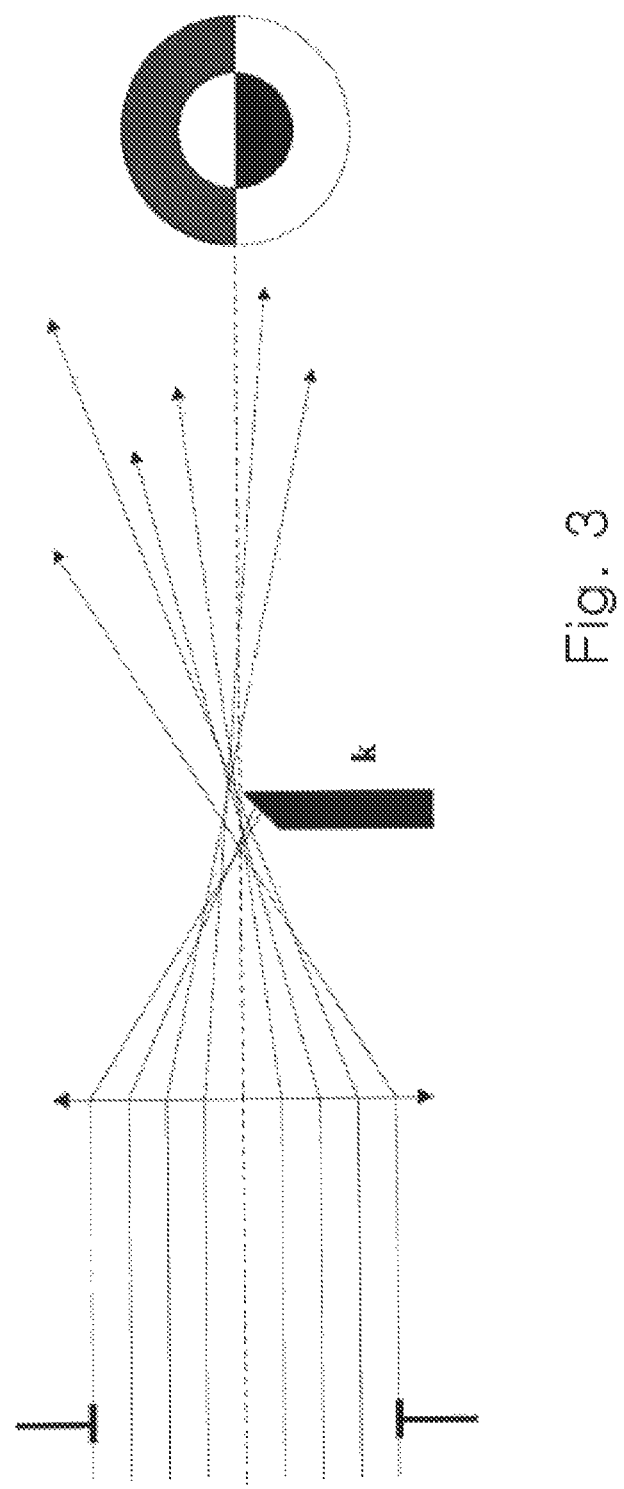

APPARATUS AND METHOD FOR MEASURING ABERRATIONS OF THE OPTICAL SYSTEM OF A LIVING BEING

CROSS-REFERENCE TO RELATED APPLICATIONS

This application is a 371 of PCT/IB2014/064958, filed Sep. 30, 2014, which claims the benefit of Italian Patent Application No. FI2013A000229, filed Oct. 2, 2013.

TECHNICAL FIELD OF THE INVENTION

The present invention refers in general to the measurement of aberrations of the optical system of a living being, in particular a human. More specifically, the invention refers to methods and systems for reconstructing a wave front and/or for building a defect or refractive error map.

The measurement of the wave front of the eye can be used to create an aberration map or elevation map of the wave front that makes it possible to evaluate aberrations along the entire optical path of the eye, comprising both internal aberrations and aberrations of the corneal surface. The aberrometric map can thus be used to calculate a surgical ablation pattern for a laser system or to design contact lenses to correct complex aberrations in the eye of the patient.

The refractive defect or vergence map is easier to understand than a wave front map for those not fully at ease with mathematical methods, for example medical staff. It clearly shows the local variations in the power of the optics system observed and therefore its defects (astigmatism, spherical aberration, coma, etc.).

BACKGROUND OF THE INVENTION

For some time apparatuses have been known for objectively measuring the visual defects of the patient, defects that are indeed known as aberrations. The apparatuses or devices used for this purpose are called aberrometers. The derivation of aberrations is equivalent to measuring the wave front coming out from the eye coming from a sharp light source arranged on the fovea. By wave front it is meant the equiphase surface of the light wave coming out from the eye.

In general the methods known up to now for measuring the wave front mainly provide for the use of sensors of two different families. The first comprises sensors adapted to estimate the aberration of the wave front from the interference pattern formed between the wave front itself and a translated version thereof. The second, on the other hand, bases its operation on the geometric optics and—given the dynamics of aberrations that it is able to measure—is the one most used in ophthalmology.

Using a rough schematisation, all of the tools adapted for measuring and characterising the reflective defect, whether they are simple auto-refractometers or more complex aberrometers, have:

1. a projection channel—the purpose of which is to create on the retina a static or dynamic light pattern—depending on the aberrometer principle used, the reflected light of which can operate as emitter;
2. an observation channel at the end of which the wave front sensor is arranged.

Taking FIG. 1 as reference, these two macro blocks are indicated with A and B.

The projection channel A comprises a light source Sa (static or dynamic, in any case able to project a point or pattern on the retina of the patient), optical elements La such as lenses or diaphragms adapted to make the appropriate projection of the light radiation produced by the source Sa, and possibly elements adapted for generating light patterns, or opto-mechanical elements adapted for moving and/or scanning images of the light source.

The observation channel B is able to collect the light projected by the projection channel A. The wave front sensor WFs and its operation are the key element of the observation channel B. Such an element, indeed, diversifies and characterises the instrument and determines its performance. Considering the wave front sensors developed up to now, all of them have a focusing optic Lb that receives the optical observation beam, for example deviated laterally by a suitable beam splitter Bc arranged on an optical axis of an eye and the retina of which is indicated with R. The optic Lb is adapted to transport the information of the wave front and focus it on a light sensor CCDb. The electrical output of the sensor is transmitted and processed by processing means in order to obtain the morphology of the wave front and the measurement of the refractive error usually through fitting algorithms of the normals of the wave front.

According to the Tscherning method the aberrometer measures the aberration of the wave front as a consequence of the first passing in the ocular medium, i.e. in the image space of the eye. A grid is projected by the projection channel and the observation channel observes the deformation of such a grid on the retina thus obtaining information on the ocular aberrations. A common variant of such a system, instead of projecting a grid on the retina, projects a set of points one after the other at great speed on parallel rays, making it simpler than the original Tscherning method to detect the spots and their deviation with respect to the ideal position.

Other types of aberrometer base their operation on the retinoscopy method, using the same operating principle as the ophthalmological examination of the same name. Retinoscopy consists of observing the apparent movement carried out by the reflected red of the ocular base; the reflection is visible in the pupil field when the eye is illuminated by a flat slit of light rays coming from infinity that is moved in a direction perpendicular to it. If the eye is myopic, the retinal image will have the image of the slit defocused and moved in a position opposite that of entry. If the eye is hypermetropic, the retinal image will have the image of the slit defocused on the same side as the entry position. The extent of the displacement will be proportional to the extent of ametropia that is measured.

The most popular wave front sensor used to detect aberrations in the human eye is, however, the Hartmann-Shack sensor (HSWS). With reference to FIGS. 2a and 2b, in this case an array of lenses is arranged with the same focal and the same diameter $D_1$ in a plane conjugated with the entry pupil of the system for which one wishes to detect the aberrations, so as to separately focus small portions of the wave front on the same image sensor.

It can be seen from the aforementioned figures how in the case of a flat wave front incident on the lenses (FIG. 2a), they will produce images with equally spaced barycentres on the plane of the detector whereas, in the case of an aberrated wave front (FIG. 2b), the local tilt of the portion of wave incident on the i-th lens of the grid will produce a movement of the barycentre of the i-th image. The simplest way to quantitatively measure this signal is to assign a quad-cell (2×2 matrix of photosensitive elements) to each sub-opening. The following quantities are defined $$\frac{\partial W}{\partial x} \propto S_x = \frac{I_2 + I_4 - I_1 - I_3}{I_1 + I_2 + I_3 + I_4}; \frac{\partial W}{\partial y} \propto S_y = \frac{I_1 + I_2 - I_3 - I_4}{I_1 + I_2 + I_3 + I_4}$$

where Ii indicates the intensity recorded by the i-th element of the quad-cell. In the absence of aberrations the image produced will be arranged symmetrically over the four elements, and therefore $S_x=S_y=0$; in the presence of aberration it is simple to show that $S_x$ and $S_y$ will be different from zero and proportional to the local spatial derivatives of the incident wave front (in the two directions of the plane).

According to all of the previous methods the wave front is obtained from the analysis of an image conjugated to the retinal plane.

Yet another type of sensor is the pyramid wave front sensor (PWS), which bases its functionality essentially on a revisitation of the Foucault knife-edge test, well known to the man skilled in the art. Such a test consists of the following steps:
1) generating a wave front from a point-shaped source;
2) inserting an opaque element into the focus of the optics system to observe what pattern the insertion of a knife creates.

Taking FIG. 3 as reference in this case, it is shown how in a wave front affected by spherical aberration the rays close to the optical axis are focused on the right of the knife k, i.e. past it, and generate a central distribution, whereas the peripheral ones are focused at a shorter distance and generate an external distribution. Like in the case of the spherical aberration, more common aberrations generate recognisable distributions, and in this way it is generally possible to determine the dominant aberration in the optics system under examination. The use of such a sensor for the purposes of measuring the human eye (which may or may not be coupled with a closed feedback system consisting of adaptive optics) has been used and studied by Iglesias and Ragazzoni in document WO2004025352. What is therein proposed is, first of all, to replace the knife with a square-based pyramid with the vertex in the same position as the knife, actually obtaining the equivalent of two simultaneous Foucault tests in a direction x and in a direction y. With reference to FIG. 4 and to the configuration indicated in it, the entering wave front creates on the CCD four images of the conjugated pupil the light intensity of which depends on the local variation of the wave front itself.

Moreover, if the operating principle of a Foucault knife is considered, it can be worked out that either lit or unlit areas become formed on the CCD, depending on whether the rays destined to such an area are or not interrupted by the presence of the knife. Every known aberration is associated with a recognisable pattern but the extent of the aberration cannot be detected: indeed, two defects of different size but the same shape generate the same distribution on the CCD. With reference to FIGS. 5a-5c, a wave front affected by 1 µm of spherical aberration (exemplified by the representation of FIG. 5a) generates a pattern like that of FIG. 5b, but the same pattern would be generated for example by a wave front affected by 10 µm of spherical aberration.

It is proposed by the same Ragazzoni, with reference to FIG. 3, to overcome this obstacle, to set the knife in motion with oscillating motion of a certain amplitude and so that the period of such oscillation is equal to the exposure time of the sensor. What is thus formed is no longer a "2-level" image but one such as to show a gradient of greys from white to black in which the value of grey is proportional to the local variation of the wave front (called local tilt) and to the size of the oscillating motion. It can be demonstrated that the introduction of such a concept, called modulation of the knife, allows the derivatives in x and in y of the wave front to be made measurable through the following formulae:

$$\frac{\partial W}{\partial x} \propto S_x = \frac{I_{1x} - I_{2x}}{I_{1x} + I_{2x}}; \frac{\partial W}{\partial y} \propto S_y = \frac{I_{1y} - I_{2y}}{I_{1y} + I_{2y}}$$

Where:
$I_{1x}$ represents the light intensity recorded on the point to be measured of the pupil determined by the knife k in horizontal motion and with k arranged to cover the left part of the beam at rest;
$I_{2x}$ represents the light intensity recorded on the point to be measured of the pupil determined by the knife k in horizontal motion and with k arranged to cover the right part of the beam at rest;
$I_{1y}$ represents the light intensity recorded on the point to be measured of the pupil determined by the knife k in vertical motion and with k arranged to cover the bottom part of the beam at rest;
$I_{2y}$ represents the light intensity recorded on the point to be measured of the pupil determined by the knife k in vertical motion and with k arranged to cover the top part of the beam at rest.

In the case of it being carried out through a pyramid-shaped prism, such formulae become:

$$\frac{\partial W}{\partial x} \propto S_x = \frac{I_2 + I_4 - I_1 - I_3}{I_1 + I_2 + I_3 + I_4}; \frac{\partial W}{\partial y} \propto S_y = \frac{I_1 + I_2 - I_3 - I_4}{I_1 + I_2 + I_3 + I_4}$$

where Ii indicates the light intensity recorded on the point to be measured of the i-th pupil determined by the pyramid. Again with reference to FIG. 5, a wave front affected by 1 µm of spherical aberration, schematised by the same representation of FIG. 5a in this way generates a similar pattern to that of FIG. 5c.

It is also demonstrated that $S_x$ and $S_y$ are proportional to the local spatial derivatives of the incident wave front with a proportionality factor also linked to the size of the modulation. Such relationships are very similar to what is found for HSWS, despite differences between the two systems that will be discussed hereafter.

In the patent document mentioned above, as well as for the first time hypothesising the use of this type of sensor for measuring the total aberration of an eye, it is made clear how the modulation can be avoided provided that a source is used that is not point-shaped but suitably extended.

Indeed, it is hypothesised to leave the pyramid static and to "oscillate the field" above the pyramid. A situation very similar to this is that of creating an extended object. It is thus shown how an optics system, in which the source is no longer point-shaped but extended and incoherent, equally makes it possible to measure the derivatives in x and in y of the wave front through a formula absolutely analogous to the one outlined above but with a proportionality factor linked no longer to the modulation but to the size of the spot on the pyramid, and consequently to the size of the spot on the retina A.

With such a clarification it can be asserted that:

$$\frac{\partial W}{\partial x} = \alpha \Delta \frac{I_2 + I_4 - I_1 - I_3}{I_1 + I_2 + I_3 + I_4}; \frac{\partial W}{\partial y} = \alpha \Delta \frac{I_1 + I_2 - I_3 - I_4}{I_1 + I_2 + I_3 + I_4}$$

Programmable elements equipped with fitting algorithms of the normals are hence able to reconstruct the wave front error or vergence error.

SUMMARY OF THE INVENTION

The Applicant has, however, now found a limitation of this type of system, a limitation not highlighted by the prior art that, assuming that the mathematical formalisation of the system itself appears exact, did not realise how the application of this type of sensor in ophthalmology leads to errors that certainly are not negligible.

According to the invention an apparatus for measuring aberrations of the optical system of a living being has the essential characteristics defined by the attached claim 1.

A further aspect of the present invention is a method as defined in claim 7.

The identification of the aforementioned limitation comes firstly from the insightful realisation that, unlike what actually happens in astronomy—the field for which the PWS was initially designed—the presence of scattering in the different ocular media expands and does not make predictable the size of the retinal spot and therefore the size of the spot on the pyramid. In particular, it should be remembered that for the formation of the apparent image of the spot on the plane of the pyramid, the scattering or dispersion in general is of the double-pass type. This is an aspect linked specifically to the system with PWS sensor, i.e. in general sensors with focal plane not conjugated to the retina, and specifically to those sensors that work on the Fourier plane, i.e. such as to focus on the light sensor a conjugated image of the pupil of the patient, given that in all systems that work with the photosensor in a plane conjugated to the retina ocular scattering is perceived as a halo around the spot or the pattern to be identified, and not as something that unrecognisably pollutes the signal.

It should be specified that by the term scattering, here and in the rest of the present description it is meant the phenomenon of deflection of the light particles due to the collision with other micro-particles present in the ocular structure. The refractive deviation of the spot from the ideal can, on the other hand, be indicated as a defocusing from aberration. Finally, the generic term dispersion is meant to indicate one of the two in an indefinite manner.

In the PWS and in all sensors that work on the Fourier plane the light reflected by the retina towards the instrument cannot be distinct from that reflected by the diffusion areas due to scattering. Such an effect in the pyramid sensor leads to the impossibility of correctly obtaining the size of the spot on the retina A and the partial derivatives of the wave front in its horizontal and vertical directions.

All this therefore translates into an intrinsic impossibility of knowing the proportionality factor that links the quantities Sx and Sy to the actual derivatives of the wave front to be measured—whether an extended source is used or modulation of the pyramid is used. A statistical approach, which assigns an average scattering value, could resize the problem for "normal" eyes, but the incidence of the phenomenon for "abnormal" eyes would remain very high. Thinking then of how much this parameter can vary in the presence of opacity such as cataracts or any other type of opacity of the ocular media, one realises how such an approach is completely inadequate.

In response to the aforementioned problem, according to the invention the way to correct the uncertainty and/or the error in the measurement is provided, also indicating how a variant of the aberrometer with pyramid sensor can also be used where necessary to measure ocular scattering.

A further result of the present invention is the definition of a specific embodiment for measuring light diffusion on the retina first, and then the aberrations, correcting the measurement with the data obtained from the measurement of the diffusion of light.

BRIEF DESCRIPTION OF THE DRAWINGS

The characteristics and advantages of the method and apparatus according to the present invention will become apparent from the following detailed description of preferred embodiments thereof, presented as an example and not for limiting purposes, with reference to the attached drawings, in which:

FIGS. 2a and 2b exemplify the operating principle of an HSWS again according to the prior art;

FIG. 3 is a representation of the operating principle of the Foucault knife for a beam affected by spherical aberration;

DETAILED DESCRIPTION OF THE INVENTION

Figure 1:
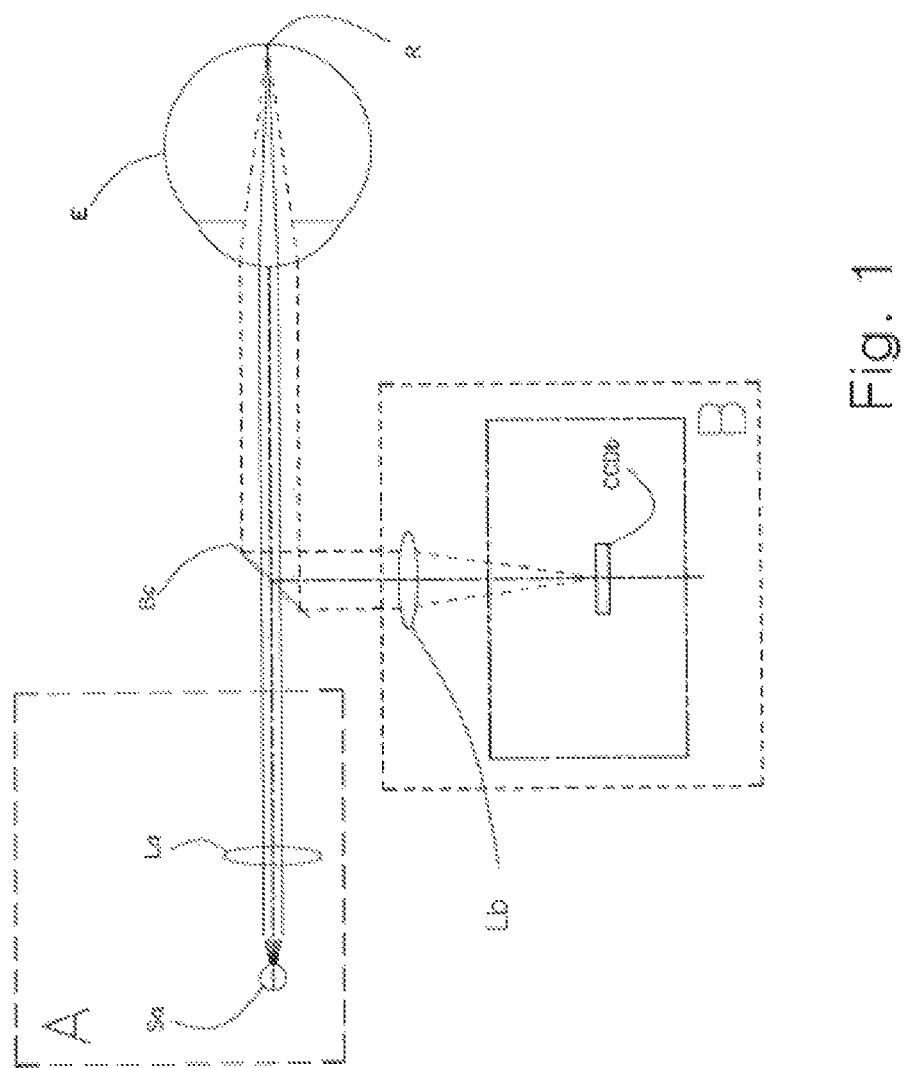
FIG. 1 is a general schematisation of an aberrometer according to the prior art.
Figure 4:
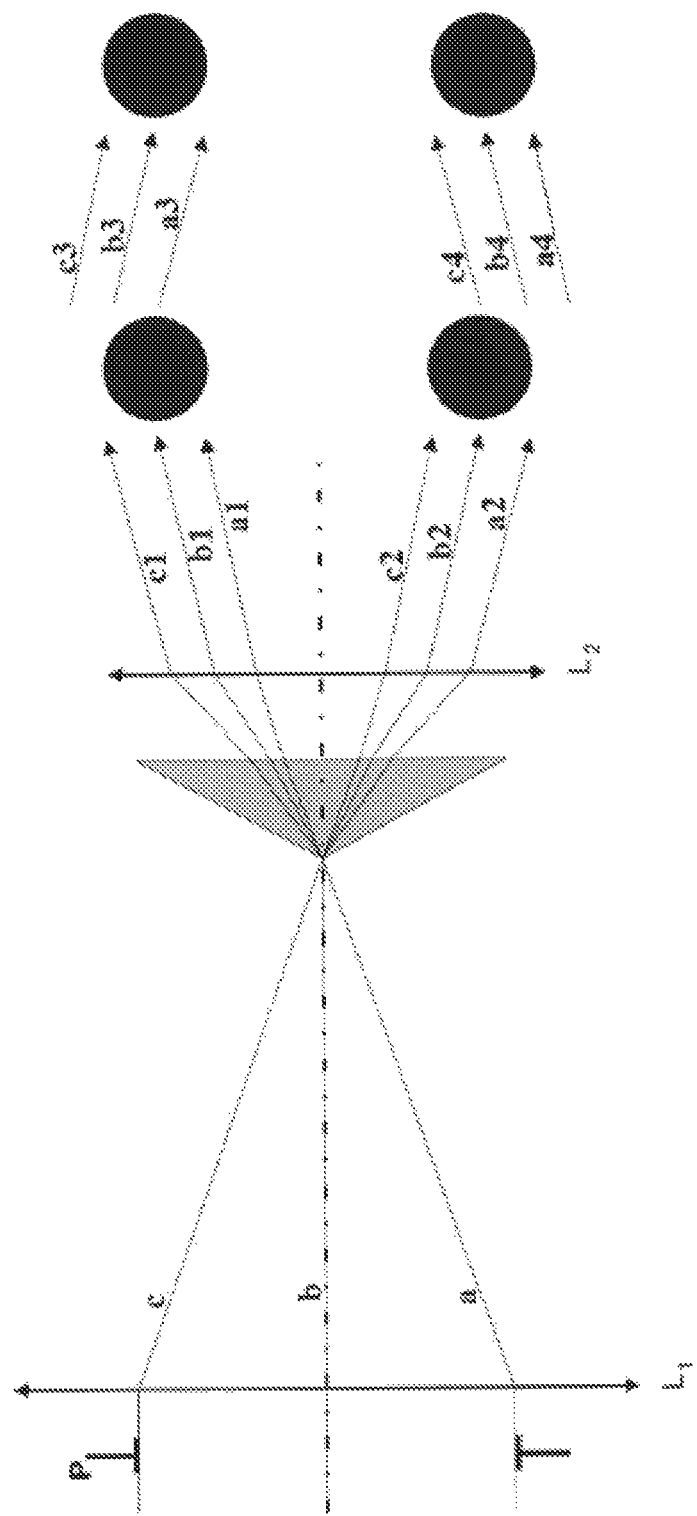
FIG. 4 exemplifies the known operating principle of a PWS in the case of a point-shaped source.
Figure 5C:
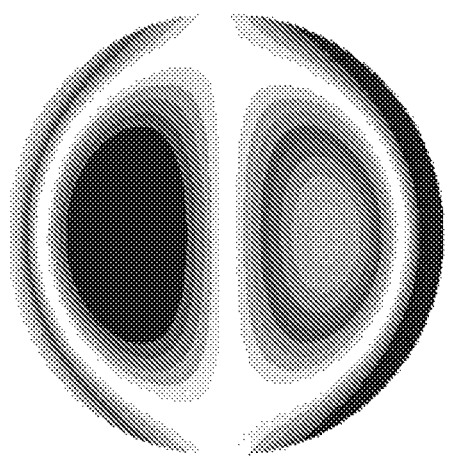
FIGS. 5a to 5c show representations of a wave front affected by spherical aberration (FIG. 5a), the aspect (FIG. 5b) of the measuring CCD carrying out the Foucault test on the wave front of FIG. 5a, and the aspect (FIG. 5c) of the measuring CCD carrying out the Foucault test on the same wave front with a suitable modulation.
Figure 5B:
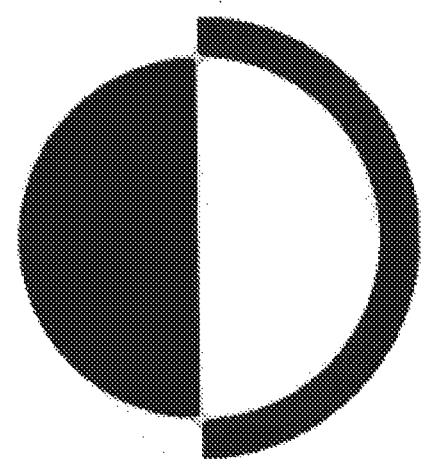
Figure 5A:
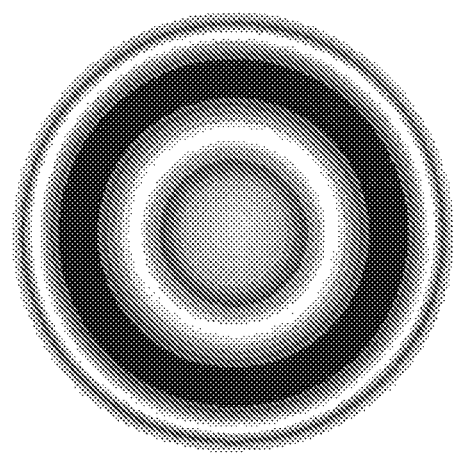
Figure 6:
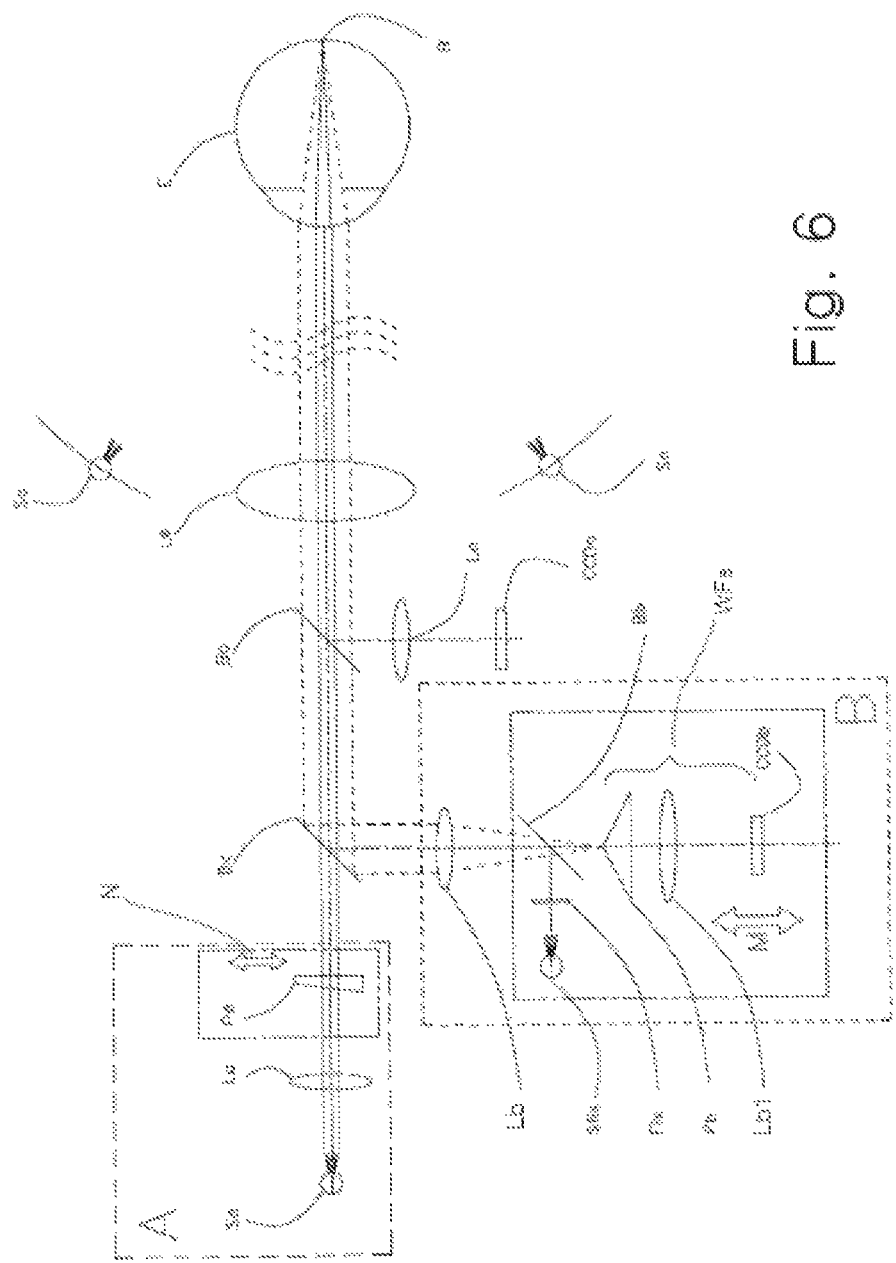
FIG. 6 is a mixed structural/functional representation of an apparatus based on PWS with measurement of the dispersion according to the invention.

With reference to FIG. 6 and from 7a to 10b, and according to what was mentioned above based on FIG. 1 (keeping the same reference symbols already used in it), an aberrometer according to the invention comprises conventional elements essentially represented by:

a projection system A of a light source on the retina;
an observation system B of the wave front containing a sensor for measuring the wave front.

As well as this, accessory components, per se known to the man skilled in the art and without a detailed description being necessary, can comprise:

a structured fixation point (Sfix, Fix);
a system for centring the eye to facilitate the alignment of the eye of the patient (So, Lo, CCDo);
a compensation system of the spherical defect of the patient to decrease the dynamics of the aberrations to be measured on the sensor (M).

During an aberrometry examination, the patient is asked to stare at a light point inside the instrument in order to align his visual axis to that of the instrument. This system consists of an illuminator (Sfix) and a sight (Fix), normally a structured one. The fixation system gives the indication to the patient of the correct direction in which to rotate the eye. As well as this, the structured sight, through its longitudinal movements, makes it possible to condition the refractive state of the patient.

In order to correctly align the gaze of the patient, a fixation system Fix is made visible to the patient through a beam splitter Bb, the optics system Lb, the beam splitter Bc and a frontal lens L0.

The frontal observation system is used by the operator to correctly line up the eye of the patient and to verify that he is staring correctly. An observation system CCDo observes, through the optic systems Lo and L0, the image of the eye illuminated by alignment light sources So in order to allow the operator easy alignment of the axis of the instrument with the centre of the pupil.

If the aberrometer is in particular of the PWS or HSWS type, in order to achieve adequate illumination, a light ray is projected on the retina through the ocular media (cornea, aqueous humour, crystalline lens, vitreous humour). A fraction of the light that arrives on the retina is retro-diffused by the retina itself and retraces its inward path in the opposite direction to generate the wave front emitted by the eye. The light emitted by the source Sa passing through the optics system La and therefore through the front lens L0, enters into the eye E of the patient and, through the pupil, generates a light spot on the retina R.

Through the optic systems L0, Lb and the beam splitter Bc the wave front for which it is wished to measure the aberrations is transferred to the wave front sensor WFs.

Figure 7A:
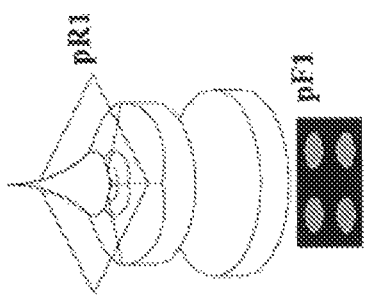
FIGS. 7a to 10b provide multiple representations (in two different views) of the retinal plane pR and Fourier plane pF in the case of 1) eye with scattering without insertion of a deviation prism (FIGS. 7a and 7b); 2) eye with scattering with prism inserted (FIGS. 8a and 8b); 3) theoretical eye without scattering without prism inserted (FIGS. 9a and 9b); 4) theoretical eye without scattering with prism inserted (FIGS. 10a and 10b).
Figure 7B:
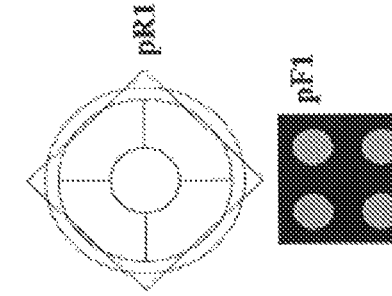
Figure 9A:
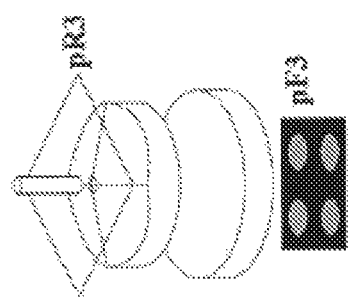
Figure 9B:
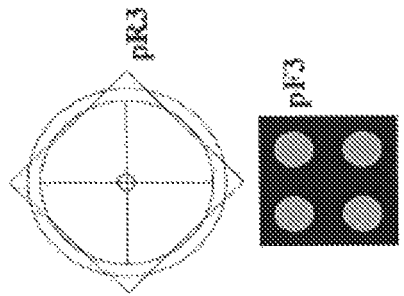

If the sensor used is a PWS, an image of the retina is created on a plane pR corresponding to the vertex of the pyramid Pb. As already explained this acts as a Foucault knife on two dimensions generating four distinct images of the pupil (or sub-pupil) that are transported on the CCDb by an optic Lb1 that focuses on the Fourier plane of the patient. On the plane of the pyramid there will be a plane conjugated to the retina and therefore in the absence of defocusing from aberrations and of dispersion by scattering the image of the emitter projected on the retina appears as pF3 in the situation of FIGS. 9a and 9b. If it is possible to be certain, at least within a certain range of approximation, that when the beam is collimated and of small dimensions the ocular aberrations do not play a very significant role (in any case producing a correctable error in feedback from an estimation of the measurement), the presence of scattering means that on the focal plane of the pyramid a situation occurs that is similar to what is represented in FIGS. 7a and 7b. This leads to an actual—and, even more seriously, unknown—decrease in sensitivity of the sensor.

According to the present invention, on the other hand, a method for measuring the dispersion is proposed, which combined with the measurement of the wave front carried out with a sensor that focuses on the Fourier plane, corrects its transduction function.

It has been stated earlier how for PWS in particular the following relationship applies:

$$\frac{\partial W}{\partial x} = \alpha \Delta \frac{I_2 + I_4 - I_1 - I_3}{I_1 + I_2 + I_3 + I_4}; \frac{\partial W}{\partial y} = \alpha \Delta \frac{I_1 + I_2 - I_3 - I_4}{I_1 + I_2 + I_3 + I_4}$$

It has also been repeated how the presence of aberrations or scattering make the quantity $\Delta$ linked to the size of the spot on the retina unknown.

By using within the apparatus, or in functional association with it, a device capable of measuring or estimating the amount of scattering in the human eye it is possible to link the output of such a device, also through a simple linear regression formula, to the value $\Delta$, thereby actually correcting the transduction function of the sensor.

Among the devices that are known as such and that in the present context can be used to quantify the scattering in the human eye, one of these, probably the simplest, consists for example of an optics system focused on the focal plane of the retina that observes the formation of a light point on it and that calculates the relationship between the energy in a central disc and that in a peripheral ring. Such a measurement provides for an estimation of how much energy is transported to the centre of the image and how much is dispersed by scattering.

In the document "An Objective Scatter Index Based on Double-Pass Retinal Images of a Point Source to Classify Cataracts" [Artal et al. February 2011; PLoS ONE; 2011, Vol. 6 Issue 2, p1] an embodiment of such a device is disclosed. Other methods are linked to the use of an HSWS as indicated in "Comparison of the retinal image quality with a Hartmann-Shack wavefront sensor and a double-pass instrument" [Diaz-Douton et al; Invest. Ophthalmol. Vis. Sci. April 2006 vol. 47 no. 41710-1716].

More advantageously, however, thinking of an apparatus according to the architecture of FIG. 6 that implements a PSW with four faces, a preferred method for quantifying the dispersion, in particular by scattering, and consequently correcting the measurement, can be described in the following terms. Considering again a situation on the focal plane of the pyramid Pb similar to that of FIGS. 7a and 7b, and calculating the amount of light in the four sub-pupils, it is found that apart from tilt phenomena, the energy contribution of the four faces will be constant.

Figure 8A:
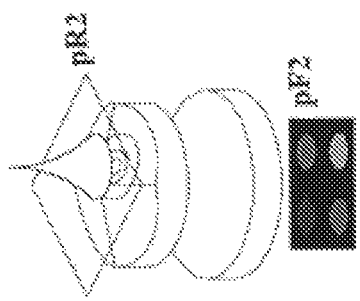
Figure 8B:
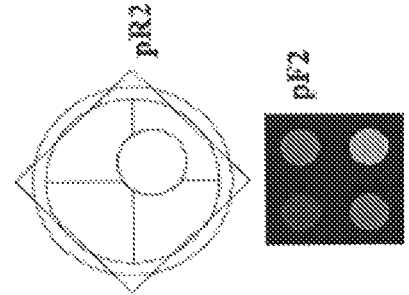
Figure 10A:
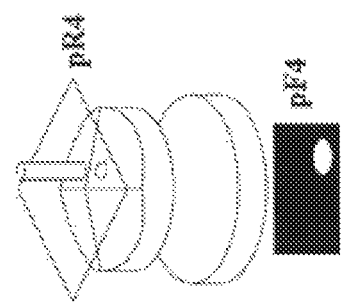
Figure 10B:
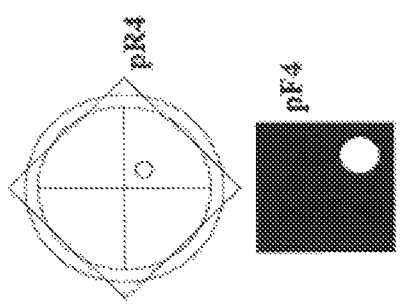

Now, assuming to insert a prism Po on the deviation path A, such that if the spot were theoretical without scattering and aberrations it would be entirely displaced on one of the four faces, all of the energy would fall on the specified sub-pupil, whereas on the other three the amount of energy would be null; such a theoretical situation is that of FIGS. 10a and 10b. In the presence of scattering, on the other hand, with an analogous insertion of the same prism, a certain amount of dispersed light will also be detected on the other three opposite faces, as highlighted by the representation on the Fourier plane pF2 in the situation according to FIGS. 8a and 8b. From the energy balance between the specified sub-pupil and the other three faces it will be possible to estimate the amount of scattering of the optics system under examination and to obtain a $\Delta$-equivalent to correct the transduction formula of the partial derivatives.

Thus, describing in greater detail a measuring procedure carried out based on what is outlined above, it is possible to identify a first step in which the patient is positioned in front of the instrument and the operator starts to carry out the alignment of the instrument with respect to the pupil of the patient. In particular according to the scheme of FIG. 6 the image of the eye can be observed through the observation system CCDo that cooperates with the alignment light sources So. Once the patient is properly aligned and in focus with respect to the instrument, or upon indication by the operator (pressing a button or whatever else), or automatically, the next step of the procedure starts. In this second step the remote point of the retina is searched for, usefully in order to free the sensor of much of the signal dynamics. In particular it is known that the aberration with the greatest dynamics in patients is the spherical defect, which can be compensated by moving the group with pyramid and CCD and associating the movement thereof with the spherical defect. In order to do this, readings of the defocus defect on the pyramid are taken in loop, and the slide on which the sensor unit is mounted is moved (movement indicated by the arrow M of FIG. 6) until the reading of such a defect on the pyramid is nullified. In such conditions the spot is minimal on the vertex of the pyramid Pb and the pyramid itself is reading all of the aberrations minus that of defocus.

If a fogging strategy is provided to eliminate the effect of proximal accommodation, it is carried out in the following conditions. A structured target (Fix+SFix) must be provided, typically integral with the position of the slide and such that it is in focus once the positioning on the remote point of the retina has been reached. Such a target is defocused in the myopic direction by a known and predetermined amount so that the patient is forced to release the accommodation.

These are the ideal conditions to carry out the acquisition, assuming the sensitivity of the instrument to be known. In order to estimate such sensitivity, a first reading of the energy balance is thus carried out on the pyramid, accumulating the energy on each of the sub-pupils, evaluating what is the global tilt at the moment of the reading [reading of 0 (zero)]. For this purpose, each sub-pupil is segmented and for each point belonging to the i-th sub-pupil the reading of the CCD is accumulated. The situation on the plane conjugated to the retina, passing through the vertex of the pyramid, is in fact that indicated by pR1 in FIGS. 7a and 7b. Having done this, the prism Po (the alternate insertion-disinsertion direction of movement of which is represented by the arrow N) is introduced on the lighting beam, so that the beam on the retina is deviated by a known amount. The movement of the prism according to the direction N can be actuated by a motor or a solenoid. In such a condition the situation on the plane of the vertex of the pyramid conjugated to the retina becomes that represented by pR2 in FIGS. 8a and 8b.

By accumulating the energy on each of the sub-pupils it is possible to make an estimation of the dispersion of the rays. Indeed, the smaller the difference between the energy accumulated on the sub-pupil of the plane pF on which the beam moved and the energy accumulated on the others, the greater the dispersion by scattering or aberrations will be. A simple law of regression, obtainable in a way that is obvious to the man skilled in the art, can link such a difference to the size of the retinal spot and to the sensitivity of the instrument that is sought. Having thus estimated the sensitivity of the instrument (sensitivity of the sensor no longer unknown but measured), it is possible to proceed to remove the prism and read the aberrations by means of the PWS as described above.

In another embodiment that is not represented graphically it is possible to include an optical component or element O having a known and measurable optical aberration, and such that its insertion can be controlled by a logic. Once the ideal situation for measuring the sensitivity of the instrument has been reached (for example after the fogging step) such an element is brought down into the observation path. Knowing that such an element has a known aberration $A_O$ it is possible to carry out the following steps in order to determine the sensitivity in the current measurement condition:

1. Carrying out an empty measurement $A^0$ presuming the sensitivity S to be known;
2. Inserting the optical element O;
3. Carrying out a measurement $A^1$ with the optical element inserted presuming the sensitivity S to be known;
4. Subtracting $A^0$ from $A^1$ one should obtain a scaled version of the known aberration introduced by O, equal to $\Delta A = A^1 - A^0 = S\mu A_O$;
5. Obtaining the sensitivity as $S\mu = \Delta A / A_O$.

It can thus be understood how thanks to the invention a substantial improvement in acquisition performance of aberrometry apparatuses like those referred to is provided, in particular making the systems with PWS sensors able to perform to their full capability, in terms of accuracy and reliability of the measurement, in the field of ophthalmology.

The present invention has been described up to here with reference to its preferred embodiments. It should be understood that each of the technical solutions implemented in the preferred embodiments described here as an example can advantageously be combined differently with each other, to create other embodiments, which derive from the same inventive core, in any case within the scope of protection of the attached claims.

The invention claimed is:

1. An analysis apparatus for measuring the aberrations of an optics ocular system of a patient, the optical system comprising a retina, the analysis apparatus comprising: a projection device (A) adapted to project a point or a pattern of light radiation on the retina of the patient; an observation device (B) comprising image sensor means having a focal plane which is not conjugated with the retina, adapted to receive the light radiation reflected by the retina; said focal plane of said image sensor means being focal plane on the Fourier plane of the patient, on which to focus a conjugated image of a pupil of said ocular system; said sensor means comprising one or more opto-mechanical elements adapted to split the image of said pupil on said Fourier plane into three or more sub-pupil images; processing means adapted to process a signal obtained from said sensor means to obtain, via a determined algorithm, a wave front and/or the refractive state generated by the optical system; the apparatus further comprising dispersion measuring means adapted to measure the dispersion of the light radiation on the retina and/or from the retina, due to scattering or aberration blurs, said processing means being configured so as to use said measure of the dispersion as a correction factor in said algorithm, wherein said dispersion measuring means comprise: optical deviation means (Po) adapted to capture a path of said light radiation in said projection device (A), to deviate of a known amount said point or pattern on the retina; and detection means for detecting a difference between the energy of the various sub-pupil images, said processing means being configured so as to obtain said correction factor from said detection.

2. An apparatus according to claim 1, wherein said at least one opto-mechanical element is a prism having a pyramid shape adapted to produce in said Fourier plane four sub-pupil images.

3. An apparatus according to claim 1, wherein said dispersion measuring means comprise an optical element (O) having a known optical aberration, adapted to capture an observation path of said light radiation in said observation device (B), said processing means being configured so as to obtain said correction factor from measurements carried out with and without said optical element (O) in said observation path.

4. An analysis method for measuring the aberrations of an optics ocular system of a patient, the optical system comprising a retina, the method comprising: projecting a point or a pattern of light radiation on the retina of the patient; observing the light radiation reflected by the retina focusing on a focal plane which is not conjugated with the retina; obtaining from said observation, via a determined algorithm, a wave front and/or the refractive state generated by the optical system; the method further providing: measuring the dispersion of the light radiation on the retina and/or from the retina, due to scattering or aberration blurs; and using said measure of the dispersion as a correction factor in said algorithm, wherein said focal plane being a focal plane on the Fourier plane of the patient, on which to focus a conjugated image of a pupil of said ocular system, and a deviation path of said light radiation is movably captured by optical deviation means (Po) to deviate said point or pattern on the retina of a known amount, and a difference is detected between the energy of the various sub-pupil images, obtaining said correction factor from said detection.

5. A method according to claim 4, wherein the image of said pupil on said Fourier plane is split into three or more sub-pupil images.

6. A method according to claim 5, wherein a prism having a pyramid shape is used for producing in said Fourier plane four sub-pupil images.

7. A method according to claim 4, wherein an observation path of said light radiation is movably captured by an optical element (O) having a known optical aberration, said correction factor being obtained from measurements carried out with and without said optical element (O) in said observation path.

* * * * *